United States Patent
Bhagat et al.

(10) Patent No.: US 10,144,009 B2
(45) Date of Patent: Dec. 4, 2018

(54) MICROFLUIDICS SORTER FOR CELL DETECTION AND ISOLATION

(71) Applicant: Clearbridge Biomedics Pte Ltd, Singapore (SG)

(72) Inventors: Ali Asgar Bhagat, Singapore (SG); Guofeng Guan, Singapore (SG)

(73) Assignee: CLEARBRIDGE BIOMEDICS PTE LTD, Singapore (SG)

( * ) Notice: Subject to any disclaimer, the term of this patent is extended or adjusted under 35 U.S.C. 154(b) by 0 days.

(21) Appl. No.: 15/029,627

(22) PCT Filed: Oct. 16, 2013

(86) PCT No.: PCT/SG2013/000442
§ 371 (c)(1),
(2) Date: Apr. 15, 2016

(87) PCT Pub. No.: WO2015/057159
PCT Pub. Date: Apr. 23, 2015

(65) Prior Publication Data
US 2016/0303565 A1    Oct. 20, 2016

(51) Int. Cl.
*G01N 15/02* (2006.01)
*B01L 99/00* (2010.01)
*B01L 3/00* (2006.01)

(52) U.S. Cl.
CPC ... *B01L 3/502761* (2013.01); *B01L 3/502776* (2013.01); *G01N 15/0255* (2013.01);
(Continued)

(58) Field of Classification Search
None
See application file for complete search history.

(56) References Cited

U.S. PATENT DOCUMENTS

| | | | |
|---|---|---|---|
| 2009/0014360 A1* | 1/2009 | Toner | B01D 21/0087 209/208 |
| 2013/0011210 A1 | 1/2013 | Toner | |
| 2013/0130226 A1 | 5/2013 | Lim | |

FOREIGN PATENT DOCUMENTS

| | | |
|---|---|---|
| JP | 2007268490 A | 10/2007 |
| JP | 2013127468 A | 6/2013 |

(Continued)

OTHER PUBLICATIONS

Japan Patent Office, Preliminary Report on Patentability (IPRP), dated Sep. 15, 2015 in PCT/SG2013/000442.
(Continued)

*Primary Examiner* — Paul S Hyun
(74) *Attorney, Agent, or Firm* — Gary M. Myles; Myles Intellectual Property Law

(57) ABSTRACT

A microfluidic device is disclosed. The device comprises at least one inlet for receiving circulating tumor cells and other cells in a sample; at least one curvilinear and/or spiral channel through which the sample is caused to undergo partial or complete Dean cycles to isolate the circulating tumor cells from the other cells; and at least one outlet configured to communicate with the channel for providing the isolated circulating tumor cells. The channel is configured to provide a predetermined Force ratio based on a desired threshold cell size of the circulating tumor cells. A corresponding method of manufacturing of the device, and a related diagnostic system are also disclosed.

15 Claims, 11 Drawing Sheets

(52) U.S. Cl.
CPC .......... *B01L 2200/0652* (2013.01); *B01L 2300/0816* (2013.01); *B01L 2300/0819* (2013.01); *B01L 2300/0861* (2013.01); *G01N 2015/0288* (2013.01)

(56) References Cited

FOREIGN PATENT DOCUMENTS

| JP | 2013521001 A | 6/2013 | |
|---|---|---|---|
| WO | 2011109762 A1 | 9/2011 | |
| WO | WO 2011109762 A1 * | 9/2011 | .......... B01L 3/50273 |

OTHER PUBLICATIONS

Japan Patent Office, International Search Report (ISR), dated Feb. 10, 2014 in PCT/SG2013/000442.

Japan Patent Office (JPO) Action dated Jul. 4, 2017 in Application No. JP2016524521 (with English Translation).

* cited by examiner

Figure 1
Figure 1a
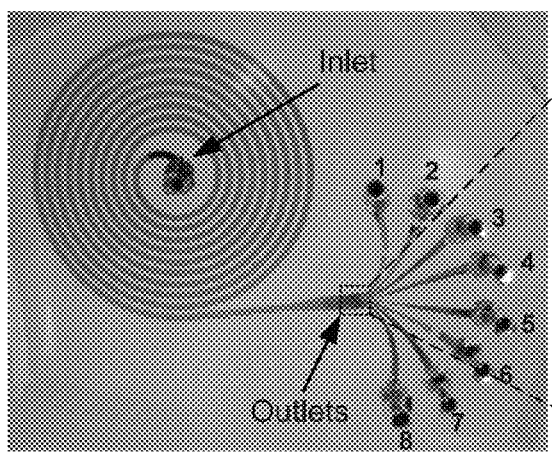
Figure 1b
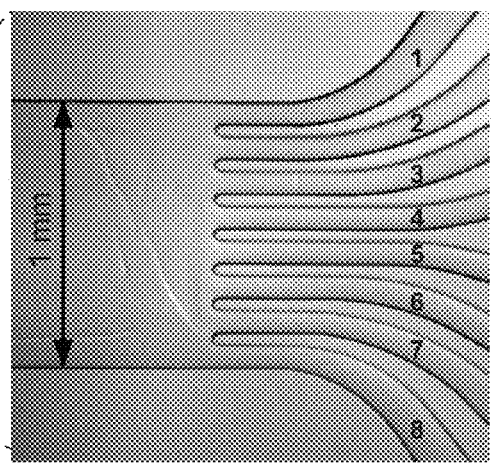

US 10,144,009 B2

MICROFLUIDICS SORTER FOR CELL DETECTION AND ISOLATION

CROSS-REFERENCE TO RELATED APPLICATIONS

This U.S. non-provisional patent application is a U.S. national stage application, which was filed on Apr. 15, 2016 under 35 U.S.C. § 371 and claims priority to PCT Patent Application No. PCT/SG2013/000442, which was filed on Oct. 16, 2013. The contents of PCT Patent Application No. PCT/SG2013/000442 are incorporated herein by reference in their entirety.

BACKGROUND

Convectional macroscale methods for separation of cells include physical filtration using membrane-based filter and density gradient centrifugation which exploit differences in cell size, deformability, and density to filter out target cells. These techniques are labor-intensive and require multi-step sample preparations which may introduce artifacts or lead to loss of desired cells. Membrane filtration methods are also easily susceptible to clogging and require frequent cleaning. Further, evidence of mechanical stress-induced changes in original phenotype of target cells subjected to filtration and centrifugation techniques has also been reported.

Hence, there is a clear need to develop simpler and more efficient techniques to process blood samples that can minimize cell loss and maintain the original target cell phenotype for subsequent analysis.

SUMMARY

Microfluidics is particularly well suited for processing blood samples primarily because of its small length scale which allows better control of the cellular microenvironment during blood separation. On-chip blood analysis has been demonstrated by several groups for different applications such as study of red blood cells (RBCs) deformability, separation of platelets and plasma, separation of leukocytes and isolation of rare cells such as CTCs or fetal cells from blood. However, a major limitation in these microfluidics systems is the low processing throughput, either due to sample dilution or due to slow flow rates, making them unsuitable for processing clinical blood samples which are usually milliliters in volume. Described herein are microfluidic devices which overcome these problems.

In a first specific expression of the invention, there is provided a method of detecting one or more circulating tumor cells (CTCs) in a sample of an individual, which includes introducing the sample into at least one inlet of a microfluidic device comprising one or more spiral channels wherein each channel has a length and a cross-section of a height and a width defining an aspect ratio adapted to isolate circulating tumor cells along portions of the cross-section of the channel based on cell size, wherein the circulating tumor cells, if present, flow along the radially innermost portion of the channel to a first outlet and other cells in the sample flow along another portion of the channel to a second outlet, thereby detecting one or more circulating tumor cells in the sample of the individual.

Embodiments may have many advantages, including continuous operation at a relatively high flow rate, enabling faster processing of clinical samples, with no chemical modification of the sample, which reduces processing time and cost, and/or the collection of viable cells for subsequent biological assays.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 1A and 1B are photographs of the fabricated spiral microchannel for CTCs isolation with a single inlet and eight equally divided outlets (labeled 1-8) fabricated in PDMS (the microchannel is filled with dye for visualization). Also shown in FIG. 1A is a microscopic image illustrating the outlet section of the spiral microchannel.

DETAILED DESCRIPTION

Figure 2:
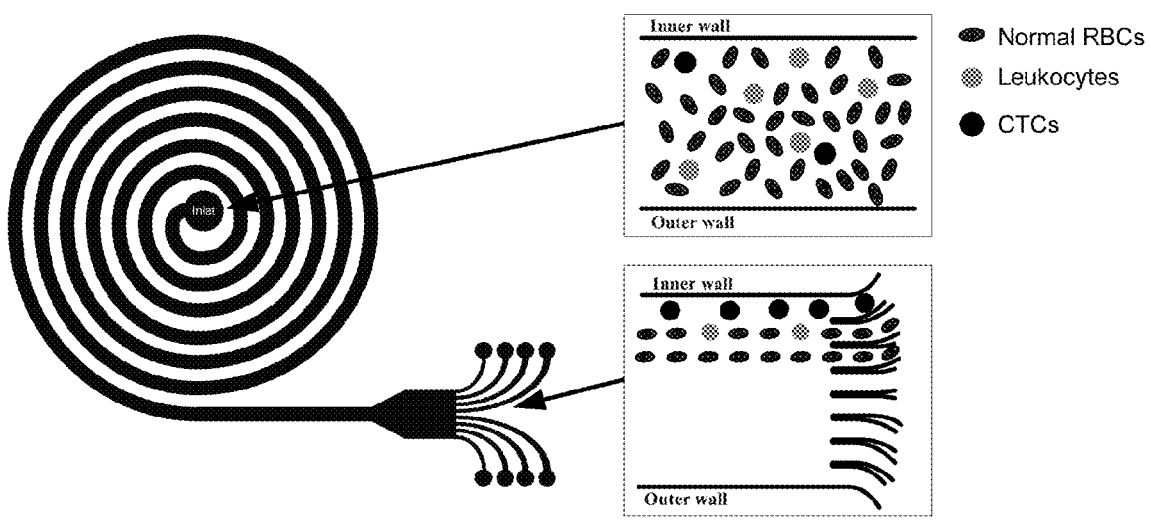
FIG. 2 is a schematic illustration of the spiral sorter for CTCs isolation. At the inlet, the blood cells (RBCs, leukocytes and CTCs) are randomly distributed across the microchannel cross-section. Under the influence of the inertial lift force and the Dean vortices, these cells equilibrate at distinct positions within the cross-section based on their size, with the larger CTCs equilibrating closest to the inner microchannel wall. The individual cell streams are then extracted using eight equally spaced outlets, achieving separation.

Embodiments may be generally directed to microfluidic devices and the use of such devices to detect and/or isolate one or more particular type of cell (e.g., target cell(s) to be detected and/or isolated) from a sample comprising 2 or more (multiple) cell types (e.g., a collection or mixture of cells). In particular, this invention may find use in many environmental and biological applications, where high resolution and high throughput for cell/particle separation are essential. More specifically, embodiments directed to microfluidic devices arranged with simple curvilinear microchannel geometry for achieving size and inertia based cell/particle separations will be described hereinafter. The microfluidic device comprises one or more inlets for introduction of the sample, one or more channels through which the sample flows, and one or more outlets, and typically at least two outlets, wherein the cells to be detected in the sample and/or isolated flow through one of the outlets (e.g., a first outlet), and the remainder of the cells in the sample do not flow through the same outlet as the cells to be isolated do, and/or flow through another (distinct) outlet (e.g., a second outlet). Each one or more channels has a length and a cross section of a height and a width defining an aspect ratio adapted to isolate the target cell(s) along at least one portion of the cross section of the channel, wherein the target cell(s) flow along a frist portion of each channel to a first outlet and the remaining cells flow along a second portion of each channel and do not flow through the same outlet as the target cell(s) and/or flow through one or more (distinct e.g., a second, third, fourth, fifth, sixth, seventh, eight, etc.) outlets.

As described herein, the microfluidic device can have one or more (at least one) inlet for introduction of the sample into the device. For example, the device can have one, two, three, four, five, six, seven, eight, nine, ten, etc., inlets.

The sample can be introduced into the device using a variety of techniques known to those of ordinary skill in the art. For example, the sample can be introduced using a syringe and/or a pump.

Similarly, the microfluidic device can have one or more outlets. In some aspects, the device can have one, two, three, four, five, six, seven, eight, nine, ten, etc., outlets. In a particular aspect, the device has at least 2 outlets. In another aspect, the device has 3 outlets. In yet another aspect, the device has 4 outlets. In still another aspect, the device has 8 outlets.

The device also comprises one or more channels (e.g., parallel channels, for example one, two, three, four, five, six, seven, eight, nine, ten, etc., parallel channels) connecting the one or more inlets to the one or more outlets. The channel(s) comprise a cross section of a height and a width defining an aspect ratio that enables separation of the target cell(s) from the remainder of the cells in the sample. As used herein, an aspect ratio is the ratio of a channel's height divided by its width and provides the appropriate cross section of the channel to allow the target cells to flow along at least one portion of the cross section of the channel to a first outlet, and the remaining cells to flow along a different (e.g., second, third, fourth, etc.) part or cross section of the channel and not to the same outlet as the target cells, such as to a distinct (e.g., second, third, fourth, etc.) outlet. The appropriate aspect ratio causes the target cells to flow along a distinct portion of the channel based on a difference in a structural characteristic of the target cell in the sample, compared to the same or similar structural characteristic of the remaining cells in the sample. Examples of such structural characteristics include cell size, stiffness, deformability, adhesiveness (e.g., cytoadhesiveness), and the like. For example, as shown herein, aspect ratios of 1, 2.5, 3.75, 5, or 7 can be used.

In a particular aspect the channel is a spiral. The height of the spiral channel can be in a range of between about 10 μm and about 200 μm, such as about 100 μm and about 140 μm. The width of the spiral channel can be in a range of between about 100 μm and about 500 μm. The length of the spiral channel can be in a range of between about 1 cm and about 100 cm.

The sample can flow through the microfluidic device at a variety of flow rates, for example physiological flow rate (e.g., physiological arteriole flow rate), or non-physiological flow rate. Example flow rates include about 20 million cells/min, or in a range of between about 2.5 mL/min and about 5 μL/min.

The microfluidic device described herein can be used to detect, separate, and/or isolate a target cell(s) from a sample of cells. The sample of cells can be, for example, a biological sample, such as blood (e.g., whole blood), plasma, peritoneal fluid, lymph, spinal fluid, urine, tissue, and the like. The sample can also be a cell culture sample. In a particular aspect, the sample is a blood sample (e.g., a whole blood sample). The blood sample can have a low hematocrit (e.g., about 1-10%), or a high hematocrit (e.g., about 20-50%).

Blood is a complex suspension of cells (~40-45% of blood volume) in plasma, which plays several key roles including transport of oxygen and nutrients to cells, removal of cellular waste products and providing immunological protection. Red blood cells (RBCs) make up for >99% of all hematologic cellular components (~$5\times10^9$ RBCs per milliliter of whole blood) with the remaining <1% consisting of peripheral blood leukocytes (PBL) and platelets. Due to its complex nature, analyzing blood using microfluidic biochips has been a challenging problem. In addition to RBCs and leukocytes, other low abundance cells such as fetal nucleated red blood cells, circulating tumor cells (CTCs), stem cells and leukemic cells are also found in the peripheral blood of patients which can be used for various biomedical applications such as patient monitoring, disease diagnosis, therapeutic treatment monitoring and conducting fundamental scientific studies. However, because these cells are extremely rare, an enrichment or separation step is almost always necessary to efficiently isolate them from blood prior to analysis.

Thus, one or more microfluidic devices (e.g., a cascade of microfluidic devices, e.g., in parallel or in sequence) described herein can be used for a variety of purposes, and, in one aspect, to detect separate and/or isolate a variety of target cells. A variety of target cells can be detected. Examples include diseased cells (e.g., diseased blood cells such as malaria-infected red blood cells, leukemic red blood cells, sickle cell anemia red blood cells, or a combination thereof, synchronized cells in an asynchronous mixture, and circulating tumor cells (CTCs)).

In another aspect, the microfluidic device can be used to detect, separate, and/or isolate circulating tumor cells. Cancer metastasis, mortal consequence of tumorigenesis, accounts for ~90% of all cancer related deaths. Specifically, viable tumor-derived epithelial cells, known as circulating tumor cells or CTCs, have been identified in peripheral blood from patients with metastatic carcinomas. These CTCs are responsible for extravasation at distant organ to form new metastatic sites and spreading cancer. Clinical reports have shown that the number of CTCs present is usually associated with disease stages and can be used as prognostic marker. Apart from prognostic significance, CTCs enumeration can also be used to assess effectiveness of therapeutic treatment and study of viable CTCs can further be useful for understanding the complex process of metastasis. That is, detection of circulating tumor cells (CTCs) which are primarily responsible for metastasis can provide valuable insights associated with disease stage and cancer progression. Their enumeration is also used for clinical evaluations and monitoring of therapeutic treatment response. As CTCs are extremely rare, comprising of as few as one cell per $10^7$-$10^9$ hematologic cells per milliliters, with highly heterogeneous morphologies and molecular signatures, their isolation from blood has been a technical challenge.

Thus, in one aspect, the invention is also directed to a method of detecting one or more circulating tumor cells in a sample of an individual. The method includes introducing the sample into at least one inlet of a microfluidic device comprising one or more spiral channels wherein each channel has a length and a cross-section of a height and a width defining an aspect ratio adapted to isolate circulating tumor cells along portions of the cross-section of the channel based on cell size, wherein the circulating tumor cells flow along the radially innermost portion of the channel to a first outlet and other cells in the sample flow along another portion of the channel to a second outlet. The method can further include collecting circulating tumor cells from the first outlet, as well as analyzing the circulating tumor cells to assess effectiveness of a therapeutic treatment. The sample can be a blood sample.

A high-throughput cell separation technique for sorting circulating tumor cells (CTCs) from blood using microfluidics is described herein. In one aspect, the design consists of low aspect ratio spirally shaped microchannels fabricated in polydimethylsiloxane (PDMS). The separation relies on the interplay between the inertial lift forces, due to the large cell size, and the Dean drag force, due to the spiral geometry, to equilibrate cells in distinct positions within the microchannel cross-section. By designing an appropriate bifurcated outlet, the cells can then be collected separately based on their size. This technique was applied to separate CTCs which are larger in size, typically ~15-20 μm in diamete, from blood cells (RBC~8 white blood cells (WBC)~8-12 μm) for early cancer detection and monitoring treatment efficiency.

Cells flowing in spiral microchannels are subjected to a combination of inertial lift forces along with the centrifugal acceleration induced Dean drag force. The inertial lift forces, which vary with the fourth power of the cell size, are responsible in focusing the cells at distinct multiple equilibrium positions within the microchannel cross-section. Adding a component of Dean drag, by designing spirally shaped microchannels, these multiple equilibrium positions can be reduced to just one near the inner microchannel wall. As the ratio of lift and Dean drag forces varies for varying cell sizes, the cells can be equilibrated at distinct positions along the microchannel cross-section based on their size, with the largest cells equilibrating closest to the microchannel wall. This results in the evolution of distinct streams of cells which can be independently collected by designing appropriate outlets.

Thus, by confining the cells suspension to the inner-half of the cross-section at the at least one inlet of the microfluidic device, and ensuring that only the larger cells are influenced by the inertial forces, while the smaller cells are influenced solely by Dean drag forces, high resolution separation can be achieved. The microchannel design parameters can be easily adjusted using a numerical model, to be described below, to change a size cut-off (i.e. cells with sizes above the size cut-off are inertial focused, while cells with sizes below the size cut-off are not), a desired channel for any type of cell/particle mixture can be readily designed and configured.

The devices are fabricated in polydimethylsiloxane (PDMS) and bonded to microscopic glass slides (FIGS. 1A and 1B). The microchannel design consists of a 500×100 μm (W×H) microchannel with an expanded 8-equally divided outlet system. The inlet samples consist of diluted whole blood (0.1% hematocrit) spiked with varying CTCs concentration. As the sample flows through the microchannel, normal RBCs, leukocytes and CTCs equilibrate across the microchannel cross-section based on their size. The CTCs, due to the large size (~15-20 μm), are significantly influenced by the inertial lift force and equilibrate close to the inner channel wall. The RBCs (~8 μm) and leukocytes (8-12 μm), which are smaller than the CTCs, are influenced more by the Dean drag and focus further away from the inner microchannel wall, thus achieving separation. By designing low aspect ratio microchannels, this difference in equilibrium positions can be amplified facilitating the collection of the rare CTCs from outlet 1, as shown in FIG. 2, with the other outlets containing the rest of the blood cells, thus achieving continuous high throughput size-based separation. In another embodiment of this technology, one could use the separation technique to isolate other rare cells including stromal cells from peritoneal fluids, leukemic cells from blood and fetal nucleated red blood cells from maternal blood.

In some embodiments, the aspect ratio of the channel is in a range of between about 1 and about 5, such as about 3.75. In certain embodiments, the method can include separating stem or precursor cells that exist within populations of mixed cell types into functionally distinct subpopulations on the basis of cell diameter. These subpopulations can then be collected from the device and analyzed in terms of unique metabolic function, for example to isolate and enrich a specific subpopulation that may have enhanced capacity to proliferate, differentiate, or respond to particular pharmaceutical agents. In certain embodiments, the width of the channel can be about 500 μm, and the height of the channel can be about 100 μm.

A high throughput size-based cell separation technique for sorting circulating tumor cells (CTCs) from whole blood using spiral microchannel geometry is described herein. The design takes advantage of the inertial lift and viscous drag forces acting on cells of various sizes to achieve differential migration. The dominant inertial forces and the Dean rotation force due to spiral microchannel geometry cause the larger CTCs to focus and occupy a single equilibrium position near the inner microchannel wall. The smaller blood components (RBCs and leukocytes) migrate to the outer half of the channel under the influence of Dean forces, resulting in the formation of two distinct streams which are then collected in two separate outlets. With the ability to process whole blood, the proposed technique takes less than 10 minutes to process 1 mL of whole blood and is able to remove 99% of hematologic cells with 90% CTC recovery in the inner outlet.

Fluid flowing through a curvilinear channel experiences centrifugal acceleration directed radially outward, leading to the formation of two counter-rotating vortices known as Dean vortices, in the top and bottom halves of the channel. The magnitude of these secondary flows is quantified by a dimensionless parameter, the Dean number (De), given by:

$$D_e = \frac{\rho U_F D_H}{\mu}\sqrt{\frac{D_H}{2R_C}} = R_e\sqrt{\frac{D_H}{2R_C}} \quad (1)$$

where ρ is the fluid density (kg/m³), $U_f$ is the average flow velocity (m/s), μ is the viscosity of the fluid (kg/ms), $R_c$ is the radius of curvature of the path of the channel (m), $D_H$ is the channel hydraulic diameter (m), and Re is the flow Reynolds number (ratio of inertial to viscous force The flow velocity is adjusted by changing the flow rates or pressure on the pumping module (eg: a Syringe pump). Thus, particles flowing in a curvilinear channel experience a drag force due to the presence of these transverse Dean flows, entraining and driving them along the direction of flow within the vortices. This motion translates to the particles moving back and forth along the channel width between the inner and outer walls with increasing downstream distance when visualized from the top or bottom. The velocity with which these cells migrate laterally when flowing in a channel is dependent on the Dean number and can be calculated using:

$$U_{Dean} = kDe^2 \frac{\mu}{\rho D_H} \text{ (m/s)} \quad (2)$$

where ρ is the fluid density (kg/m³), μ is the viscosity of the fluid (kg/ms), DH is the channel hydraulic diameter (m) and k is a scaling factor determined empirically for these curvilinear channels as approximately ~0.01 and verified using COMSOL models of these channels.

The lateral distance traversed by a particle along the Dean vortex can be defined in terms of 'Dean cycle'. For example, a particle which is initially positioned near the microchannel inner wall and migrates to the channel outer wall at a given distance downstream is said to have completed ½ a Dean cycle. Returning back to the original position near the microchannel inner wall completes a full Dean cycle. For a given microchannel length, the particles can thus undergo multiple Dean cycle migration with increasing flow rate (Re) conditions. The length for a complete Dean cycle migration can be calculated as:

$$L_{DC} \sim 2w+h(m) \quad (3)$$

where w is the microchannel width (m) and h is the microchannel height (m). Consequently, the total microchannel length required for Dean migration is given by:

$$L_C = \frac{U_f}{U_{Dean}} \times L_{DC} \text{ (m)} \quad (4)$$

It is to be appreciated that the magnitude of Dean drag force is given by the Stokes' law:

$$F_D = 3\pi\mu U_{Dean} a_c (N) \quad (5)$$

where $a_c$ is the cell diameter (m).

Apart from the Dean drag force, larger cells with diameter comparable to the microchannel dimensions also experience appreciable inertial lift forces ($F_L$) (both shear and wall-induced) resulting in their focusing and equilibration. The parabolic velocity profile in Poiseuille flow results in a shear-induced inertial lift force $F_{IL}$ acting on the particles directing them away from the microchannel center towards the channel walls. As these particles move closer to the channel wall, the abrupt presence of the wall disrupts the rotational wake formed around the particles inducing a lift-force ($F_{WL}$) directing them away from the wall, towards the microchannel center. As a result of these two opposing lift forces, the particles equilibrate (focus) around the microchannel periphery at distinct and predictable positions. This effect is dominant for particles with size comparable to microchannel dimensions $a_c/h$~0.1. Particularly, the magnitude of the inertial lift force ($F_L$) is given by:

$$F_L = C_L \rho G^2 a_c^4 (N) \quad (6)$$

where $C_L$ is the lift coefficient which is a function of the particle position across the channel cross-section assuming an average value of 0.5, and G is the shear rate of the fluid (1/s). The average value of G for a Poiseuille flow is given by $G=U_{max}/D_H$, where, $U_{max}$ is the maximum fluid velocity (m/s) and can be approximated as $2 \times U_F$. Accordingly, the inertial lift force ($F_L$) of equation (6) above can then be re-expressed as:

$$F_L = \frac{2\rho U_F^2 a_c^4}{D_H^2} \text{ (N)} \quad (7)$$

In microchannels with curvilinear geometry, the interplay between the inertial lift force ($F_L$) and the Dean drag force ($F_D$) reduces the equilibrium positions to just two near the inner channel wall, each within the top and bottom Dean vortex. The two equilibrium positions overlay each other along the microchannel height and are located at the same distance from the microchannel inner wall for a given particle size, i.e., viewed as a single position across the microchannel width.

Taking advantage of these two phenomena, i.e. Dean migration and inertial focusing, particles and cell mixtures of varying sizes can then be separated. The dimensions of the microchannel parameters (i.e. width, height, length, radius of curvature and flow rate) are chosen based on the mathematical models afore described to ensure that the larger cells/particles undergo inertial focusing while the smaller cells/particles (below the size cut-off) do not experience the focusing effect. At the inlet the cell/particle mixture is confined near the inner wall of the microchannel, and as the cells/particles move downstream, the smaller particles are transposed to the other half of the channel cross-section under the influence of Dean drag forces. On the other hand, cells/particles above the size cut-off experience strong inertial lift forces and remain focused near the inner channel wall. Thus at the outlet, the smaller cells/particles can be collected from a small cell outlet while the larger cells/particles can be collected from a large cell outlet, thereby achieving separation and isolation. The cut-off of the size can be estimated by the ratio of the two forces (i.e. the inertial lift force ($F_L$) and the Dean drag force ($F_D$)):

$$i_F = F_L/F_D = \frac{85.11 R_C a_C^3}{D_H^4} = \frac{85.11 R_C a_C^3}{h^4} \quad (8)$$

where $i_F$ is the Force ratio, and the remaining parameters are to be understood as per the foregoing defined in equations (1), (5) and (6). The flow density (ρ) and fluid viscosity (μ) refers to the combined density and viscosity. We can adjust either the sheath or sample to adjust the final fluid density and viscosity. According to experimental data obtained, the threshold for $i_F$ is ~2 for inertial focusing of particles/cells.

For test conditions of $i_F$ less than 2, the particles/cells are only influenced by the Dean drag force and thus circulate with the Dean flow. That is, for the particles/cells to undergo inertial focusing, $i_F$ is to be greater or equal to 2 (i.e. $i_F \geq 2$). It can be seen that the Force ratio, $i_F$, thus acts as a threshold factor to determine whether the particles/cells undergo inertial focusing. From equation (8), it can be seen that $i_F$ is determined by several parameters, such as the radius of curvature, a diameter of the particle/cell (i.e. cell/particle size) as well as the hydraulic diameter.

Among these parameters, the hydraulic diameter and the size of the particle/cell have the most significant affect on determining whether or not a cell/particle experiences inertial focusing. Since low aspect ratio rectangular cross-section channel are to be used for the separation, the channel height h is an important parameter to determine whether a particle/cell with a known diameter can be focused at the side of the channel or will travel along the Dean flow (DH can be substituted by h in low aspect ratio channels). Accordingly, within the size range of the particle/cell of interest, it is reasonable to select the channel height to be $h < 10 \times a_c$ for those particles/cells that are required to be focused at the inner side of the channel.

Following from the above, it is to be highlighted that the work described herein takes advantage of those two phenomena, i.e., Dean migration and inertial focusing, to demonstrate its ability for isolating CTCs from blood. More specifically, a size-based separation method for CTCs separation and isolation from blood in a microfluidic device will be described hereinafter, which works by exploiting the size difference between the CTCs, and the other blood cells (as already mentioned above). It is to be highlighted that the proposed device is capable of achieving ultra-high purity compared to existing CTC separation technologies with a $5*\log_{10}$ depletion of WBCs.

Figure 3:
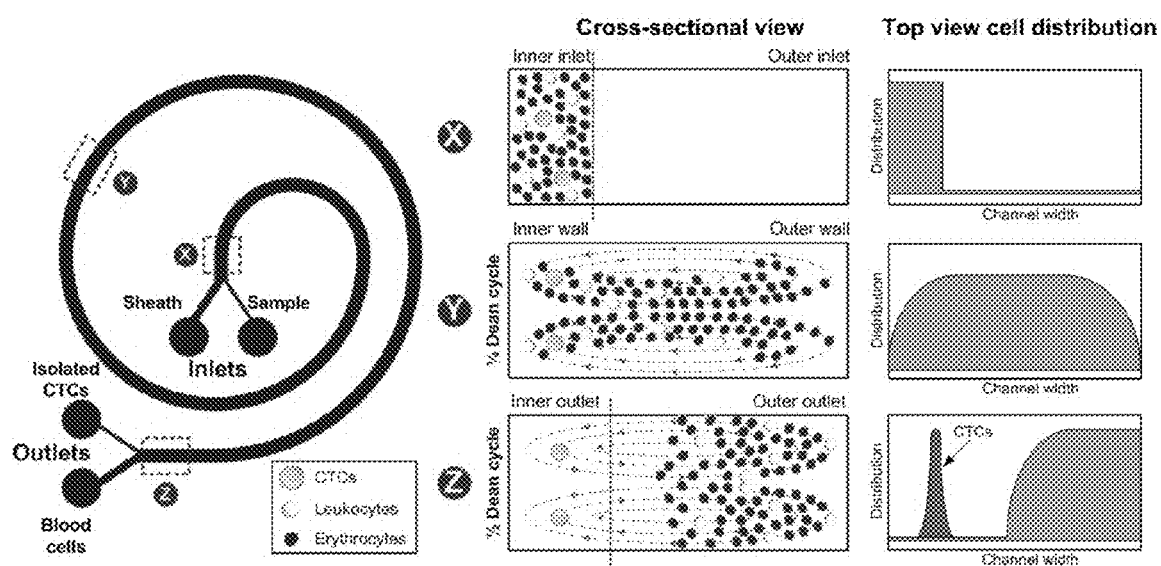
FIG. 3 is a schematic of the developed ultra-high throughput CTC isolation chip illustrating the operating principle. Whole blood is pumped through the inner inlet of the device while sheath fluid is passed through the outer inlet. Under the influence of Dean drag forces, due to the curvilinear channel geometry, the smaller hematologic cells (RBCs and WBCs) migrate out towards the channel outer wall following the two counter rotating vortices (cross-sectional view). The CTCs, due to their larger size. experience strong inertial lift forces equilibrating them along the microchannel inner wall, thus achieving separation.
Figure 4A:
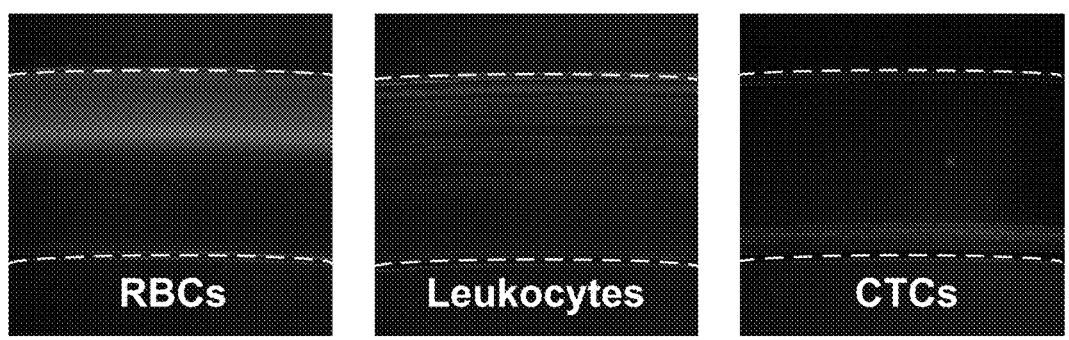
FIGS. 4A and 4B are average composite images 4A and linescans 4B, indicating the lateral positions of the RBCs, leukocytes and CTCs at the outlet of the spiral microchannel. The images show that the hematologic cells (RBCs and leukocytes) are transposed to the outer half of the channel under the influence of Dean drag forces while the larger CTCs focus closer to the channel inner wall under the influence of inertial lift forces.
Figure 4B:
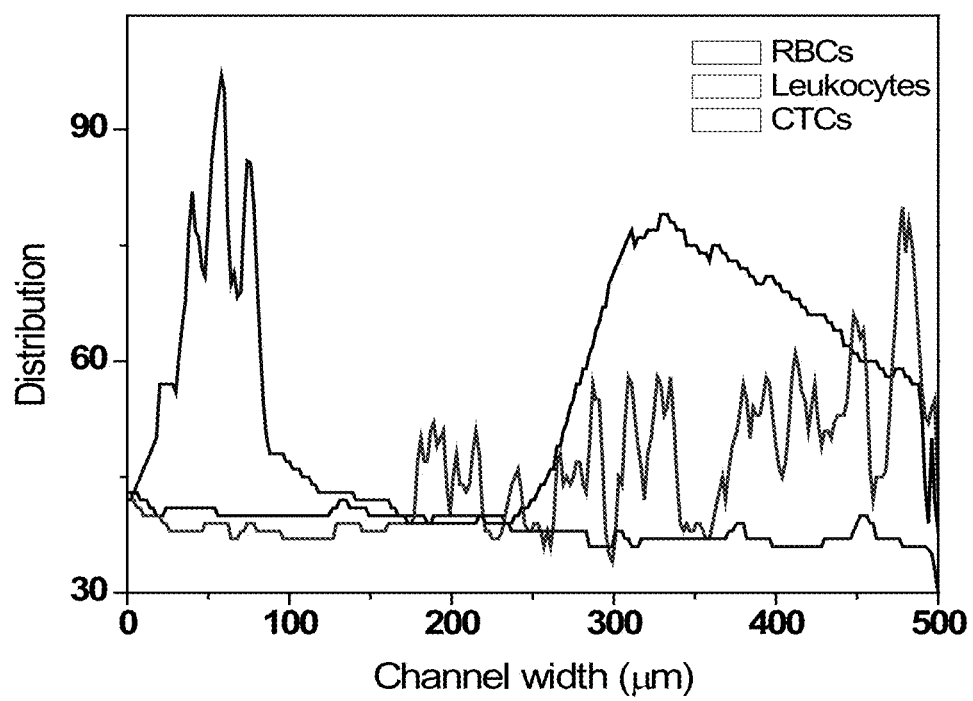

In one aspect, the design comprises a 2-inlet 2-outlet spiral microchannel with a total length of ~10 cm. The microchannel width is about 500 μm and the height is about 140 μm. As shown in FIGS. 4A and 4B, the channel dimensions are selected such that the larger CTCs undergo inertial focusing, while the migration of the smaller hematologic cells (RBCs and leukocytes) is affected by the Dean drag (i.e., only the CTCs satisfy the $a_c/h \sim 0.1$ ratio). At the inlet, whole blood sample is pumped into the inner inlet and sheath fluid (e.g., 1×PBS) through the outer inlet of a spiral microchannel (FIG. 3). Sheath fluid can be used to pinch the whole blood at the inlet, to confine the whole blood sample to a narrow region across the channel width, so that all the cells start to migrate from approximately the same location. During testing, under the influence of the Dean drag forces, the small cells initiate migration along the Dean vortex and move towards the channel outer wall. The strong inertial lift force experienced by the CTCs prevent them from migrating under the influence of Dean drag and cause them to focus and occupy the two equilibrium positions near the microchannel inner wall. On the other hand, since the RBCs and leukocytes are not influenced by the inertial forces, these cells continue to circulate along the Dean vortex. By calculating the appropriate flow rate ensuring that the cells undergo half Dean cycle migration, at the outlet, the CTCs focus near the channel inner walls while the RBCs and leukocytes are transposed to the outer half of the channel. Thus, the CTCs can be isolated and collected at the inner outlet while the other blood cells are collected at the outer outlet (FIG. 3). The advantage of using this technique is its ability to process very high hematocrit samples (whole blood) thus reducing sample preparatory steps and decreasing the analysis time significantly. Using this technique, 1 mL of whole blood can be processed in under 10 minutes.

Figures 5, 5A, 5B, 5C, 5D:
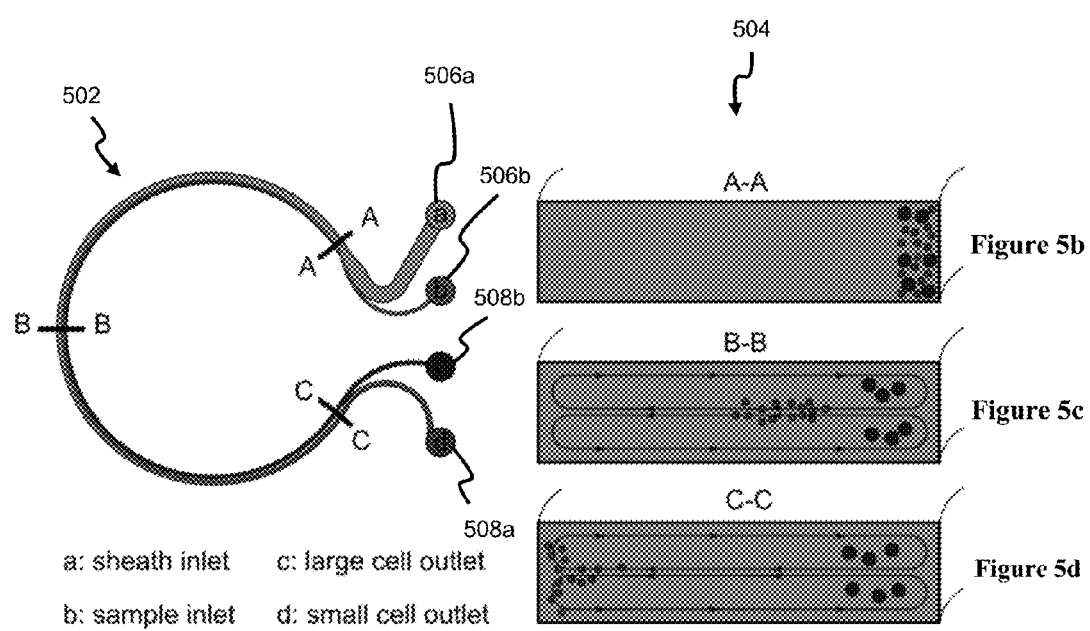
FIG. 5 includes FIGS. 5a-5d showing a top view of a curvilinear channel of a microfluidic device and accompanying diagrams to illustrate a process of isolating cells by applying the principles of half Dean cycle for cell separation, in accordance with one embodiment.

In another different aspect, another design is depicted in FIG. 5a, which shows a top view of a curvilinear microchannel 502 of a microfluidic device (not shown), and accompanying diagrams to illustrate a process 504 of isolating cells by applying the principles of half Dean cycle. More specifically, the curvilinear microchannel 502, as the term suggests, is formed of a single curvilinear microchannel section having a sheath inlet 506a, a sample inlet 506b, and two outlets being termed as a small cells outlet 508a, and a large cells outlet 508b. Moreover, the curvilinear microchannel 502 has a generally C-shaped arrangement. To isolate and enrich CTCs from the blood (i.e. a sample) of an individual using the curvilinear microchannel 502, the curvilinear microchannel 502 is selected with an $R_C$ of 1.5 cm and a total length of ~10 cm, with reference to equation (8). In addition, the width and height of the curvilinear microchannel 502 are also selected to be 600 μm and 160 μm respectively. Particularly, the above dimensions of the curvilinear microchannel 502 are purposefully selected such that only the larger CTCs undergo inertial focusing, while the smaller hematologic cells (RBCs and leukocytes) are affected by the Dean drag, as will be appreciated.

Accordingly, the process 504 is started by introducing the entire blood sample through the sample inlet 506b and a sheath fluid (e.g. 1×PBS) through the sheath inlet 506a of the curvilinear microchannel 502 (i.e. see FIG. 5a). Initially, the cell/particle mixture is confined to a side near the inner walls of the curvilinear microchannel 502 and remains fairly homogenously mixed, as depicted at a section A-A of the curvilinear microchannel 502 in FIG. 5b. As the cells/particles travel further downstream, the smaller cells/particles are more strongly affected by the secondary Dean flows and travel towards a side near the outer walls (which are opposite to the inner walls) of the curvilinear microchannel 502, while the bigger cells/particles remains near the side of the inner walls (as they are focused under the effect of inertial lift forces), as depicted at a section B-B of the curvilinear microchannel 502 in FIG. 5c. It will be appreciated that the inner walls are radially closer to an imaginary centre of a circle formed by the curvilinear microchannel 502 than the outer walls. That is to say, under the influence of the Dean drag forces, all the small cells initiate migration along with the Dean vortex and move towards the outer walls. But the strong inertial lift forces experienced by the CTCs prevent them from migrating under the influence of Dean drag, causing the CTCs to be focused, and occupy the two equilibrium positions near the inner walls. On the other hand, since the RBCs and leukocytes are not influenced by the inertial forces, these cells continue to circulate along with the Dean vortex. Hence, by calculating and selecting an appropriate flow rate to ensure that the cells undergo half Dean cycle migration, by the time the flow reaches the two outlets, the CTCs are made to focus near the inner walls, whereas the RBCs and leukocytes are transposed to the outer walls. That is, the sample undergoes only half a Dean cycle in the curvilinear microchannel 502 for this design.

Thus, by designing the appropriate channel length for a selected flow rate, the targets cells/particles can consequently be completed separated from non-target cells/particles (i.e. see section C-C of the curvilinear microchannel 502 in FIG. 5d) and collected using the various different outlets. As will be appreciated, the CTCs can be isolated and collected at the large cells outlet 508b, and the other blood cells are collected at the small cells outlet 508a. The advantage of using a shorter length lies in the ability to process the blood sample at extremely high flow rates, thus translating to larger blood volumes being processed, which is an important consideration for any rare cell isolation technique. As an example, using this technique, 8 mL of blood can be processed in about within 10 minutes. Importantly, this may be the fastest processing speed demonstrated in microfluidics systems till date, as will be appreciated. It also allows multiplexing of channels in the same plane in a back to back configuration.

Figure 6:
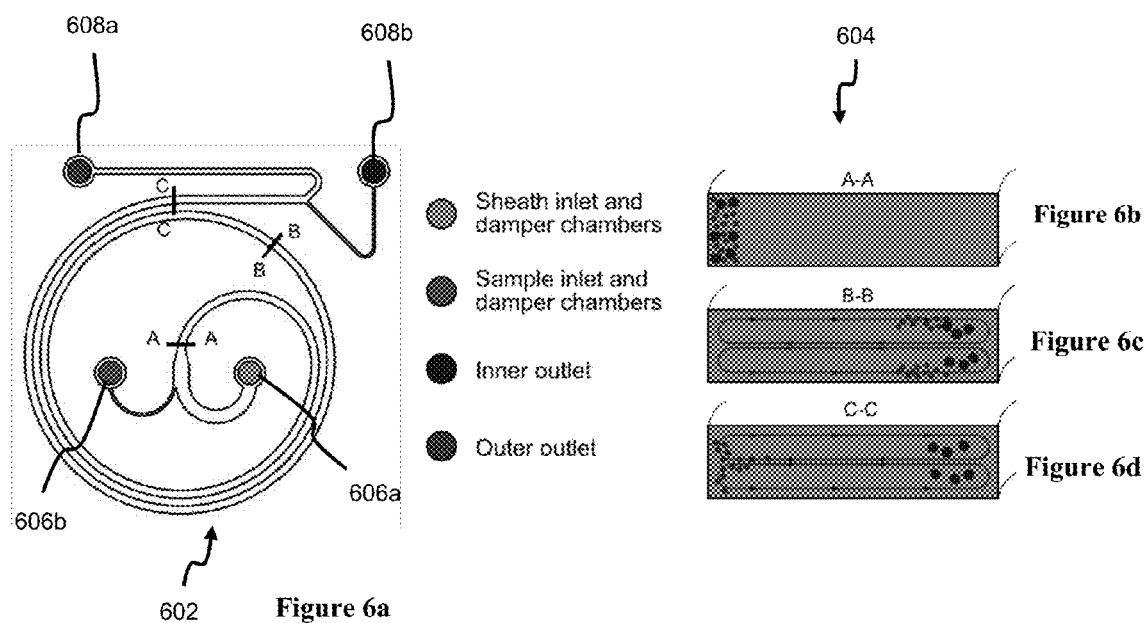
FIG. 6 includes FIGS. 6a-6d showing a top view of a spiral channel of a microfluidic device and accompanying diagrams to illustrate a process of isolating cells by applying the principles of a one complete Dean cycle, in accordance with another embodiment.

In a further aspect, an alternative design is shown in FIG. 6a, which shows a top view of a spiral microchannel 602 of a microfluidic device (not shown), and accompanying diagrams to illustrate a process 604 of isolating cells by applying the principles of one complete Dean cycle for cell separation. The microfluidic device is realized in the form of a proposed biochip (not shown) for isolating and enriching CTCs from the blood (i.e. a sample) of an individual. In this instance, the spiral microchannel 602 is formed of a single curvilinear microchannel section of a substantial length (relative to the curvilinear microchannel 502 of FIG. 5a) to form a spiral formation, and is arranged with a sheath inlet 606a, a sample inlet 606b, and two outlets termed as a small cells outlet 608a, and a large cells outlet 608b. The small cells outlet 608a and large cells outlet 608b are also termed as outer and inner outlets respectively. From the top view, the sample inlet 606b is positioned to the left of the sheath inlet 606a, while the small cells outlet 608a is positioned to the left of the large cells outlet 608b. This arrangement specifically ensures that any sample introduced into the spiral microchannel 602 will initially flow along a side near the outer walls of the spiral microchannel 602 than along a side near the inner walls thereof. It will be appreciated that the outer walls are radially further than the outer walls to an imaginary centre of a circle formed by the spiral microchannel 602. In addition, the sheath inlet 606a and sample inlet 606b are both coupled to damper chambers (not shown), and are also arranged substantially in the centre of the spiral microchannel 602, as can be seen from FIG. 6a. The damper chambers are specifically for regulating flow rates of the sheath fluid and sample introduced respectively via the sheath inlet 606a and sample inlet 606b to get stable laminar fluid streams within the microchannels. This may be important where the type of pump used is a peristaltic pump as discussed below. The small cells outlet 608a and large cells outlet 608b, on the other hand, are arranged external to the spiral microchannel 602.

With reference to equation (8), the spiral microchannel 602 is then desirably selected with an $R_C$ of 1.0 cm, with the width and height of the spiral microchannel 602 selected to be 500 µm and 175 µm respectively, with length 10 cm. Accordingly, based on equation (8) taking into account the selected parameters, this then gives a Force ratio, $i_F$, of 3.06 for 15 µm polystyrene particles (representative of CTCs), and 0.91 for 10 µm particles (Polystyrene particles representative of WBCs) at a sample flow rate of 100 µL/min and a sheath flow rate of 800 µL/min, as per equation (8). Needless to say, the above dimensions of the spiral microchannel 602 are selected in order that only the larger CTCs undergo inertial focusing, while the migration of the smaller hematologic cells (RBCs and leukocytes) is solely affected by the Dean drag.

The process 604 starts by introducing the blood sample through the sample inlet 606b and the sheath fluid through the sheath inlet 606a, which causes the blood sample to initially flow along a side near the outer walls of the spiral microchannel 602, (as aforementioned). The cells will align substantially close to the outer walls with the help of the sheath fluid, as shown at a section A-A of the spiral microchannel 602 in FIG. 6b. After half of the Dean cycle, both large and small cells will have traveled to a side near to the inner walls of the spiral microchannel 602 (i.e. see section B-B of the spiral microchannel 602 in FIG. 6c). By the time the flow reaches the end of the length of the spiral microchannel 602, the smaller cells have finished one cycle along with the Dean cycle, while the larger cells maintain focused along the inner walls (i.e. see section C-C of the spiral microchannel 602 in FIG. 6d).

The process 604 in this instance thus, instead of causing the large cells to be focused along a side of the inner wall at the beginning (as per the process 504 of FIGS. 5b-5d), causes all of the cells to travel from a side of the outer walls to a side of the inner walls, but with an effect however that the small cells will finish a whole Dean cycle to return to the side at the outer walls again by the time the flow reaches the end of the spiral microchannel 602. That is, the sample undergoes a complete Dean cycle in the spiral microchannel 602 for this design. With this design, a longer channel length and a lower flow rate are required, which is appropriate for the separation of shear sensitive cells. The fully developed flow may also improve the CTC focusing quality as well as increase the distance among the cells of critical size to obtain a better cell separation. Also, in this embodiment, the small cells outlet 608a and large cells outlet 608b are each configured with respective width and length that are optimized to adjust the flow resistance at the small cells outlet 608a and large cells outlet 608b, and a volume ratio of collection. This is further supplemented through use of the damper chambers. Particularly, a length and a width of the large cells outlet 608b are selected to be 18 mm and 350 µm respectively. On the other hand, a length and a width of the small cells outlet 608a are selected to be 10 mm and 150 µm. As a result, a volume ratio between the collections at the small cells outlet 608a and large cells outlet 608b is then accordingly found to be about 2.85±0.20. As a guideline to facilitate selection of parameters for configuring dimensions of microchannels (of microfluidic devices) to enable separation of CTCs from blood cells, with reference to FIGS. 5a and 6a, it is thus proposed that a height of the microchannel 502, 602 is selected to be in a range of about 120 µm to 180 µm, whereas a width of the microchannel 502, 602 is to be selected to be in a range of about 300 µm to 650 µm, and a radius of curvature of the microchannel 502, 602 is to be selected to be between 5 mm to 20 mm, depending on the cell size of the CTCs to be isolated.

Figure 7:
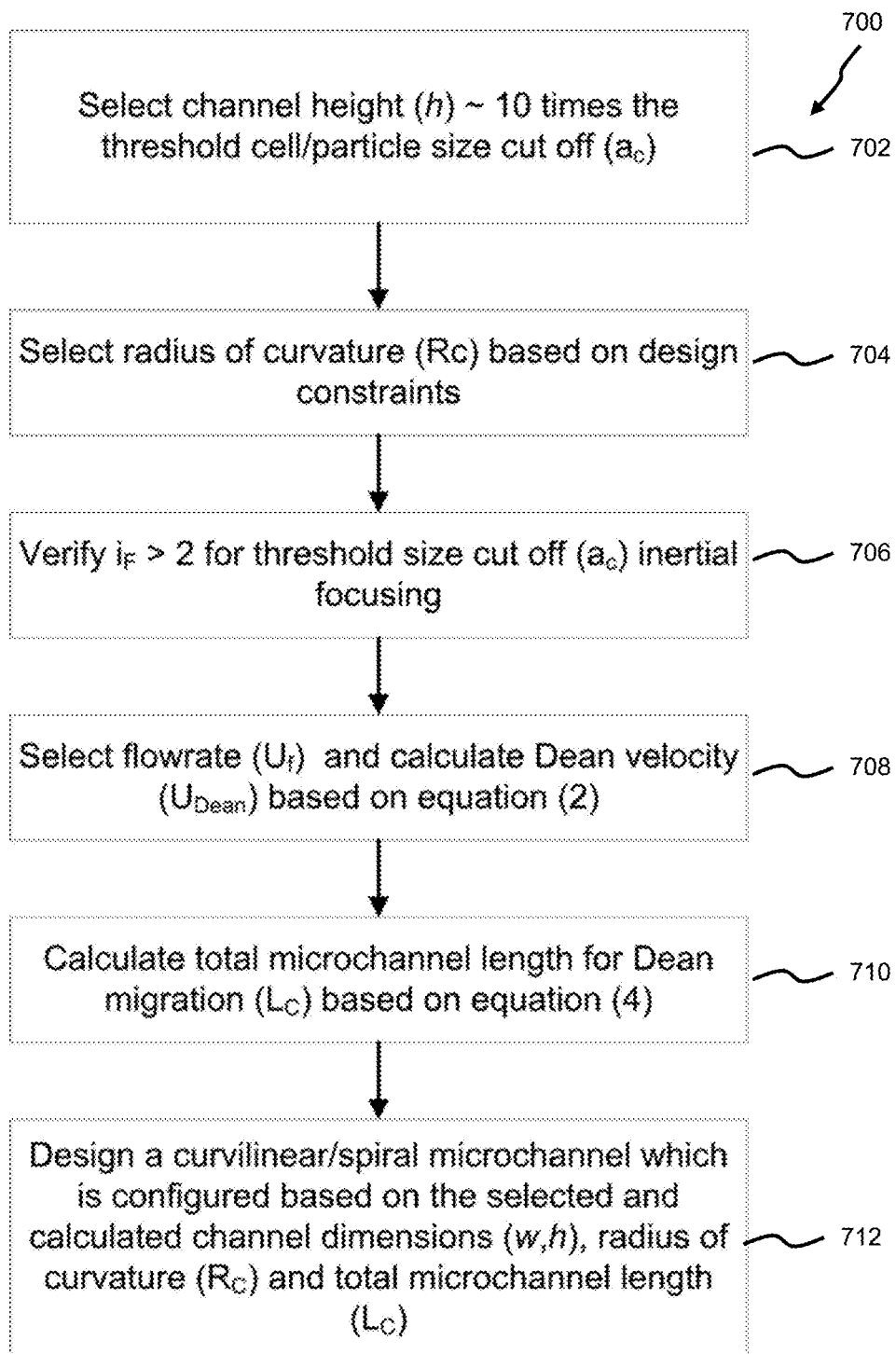
FIG. 7 is a flow diagram of a method of manufacturing the microfluidic device of FIG. 5a or 6a adapted for isolating CTCs from other cells in a sample.

FIG. 7 depicts a flow diagram of a method 700 of manufacturing the microfluidic device of FIG. 5a or 6a adapted for isolating CTCs from other cells in a sample (e.g. blood sample). Broadly, we select the hydraulic diameter (Dh) to be ~10 times the cell size cut-off 702. In the case of CTCs, the size cut-off is 15 µm and hence the diameter is ~150 µm. The range of width and heights are then selected to achieve this diameter. The radius of curvature can be first selected 704 based on considerations including but not limited to—

1. Real estate at the center of the channel to accommodate inputs
2. Manufacturing ability
3. Length of the microchannel required ($2\pi Rc$)

Then equation (8) can be used 706 to determine if the force ration is above 2. The velocity is selected 708 based on equation (2). The microchannel length is selected 710 based on equation (4). Then the microchannel can be designed 712 based on the channel dimensions (w,h), radious of curvature ($R_C$) and length ($L_C$).

It is to be appreciated that the above described microfluidic device of FIG. 5a having the curvilinear microchannel 502 and the microfluidic device of FIG. 6a having the spiral microchannel 602 may be implemented as respective biochips in a form factor (e.g. as a disposable cartridge) suitable for replaceable use in a related diagnostic system (not shown) that is specifically configured for cells/particles (e.g. CTCs) isolation and detection. In particular, there may be different various biochips configured for use depending on the type of cells/particles to be isolated. Also, biochips in use may be discarded and replaced after a one time usage to prevent sample contamination in subsequent analysis, and new biochips are swapped in, the operation of which will be apparent to skilled persons. In addition, the diagnostic system includes a processor to generate a diagnostic reading based on a detected amount of the circulating tumor cells isolated by the biochips, and also further includes a flow regulator for adjusting a fluid velocity of a sample flowing through the microfluidic device (in accordance with equation (8) for inertial focusing the circulating tumor cells). Based on the type of cells/particles to be isolated and detected, other different controlling attributes (e.g. determining a flow velocity of a sample) of the diagnostic system may be appropriately adjusted to achieve the necessary object, as it will be appreciated.

Figure 9:
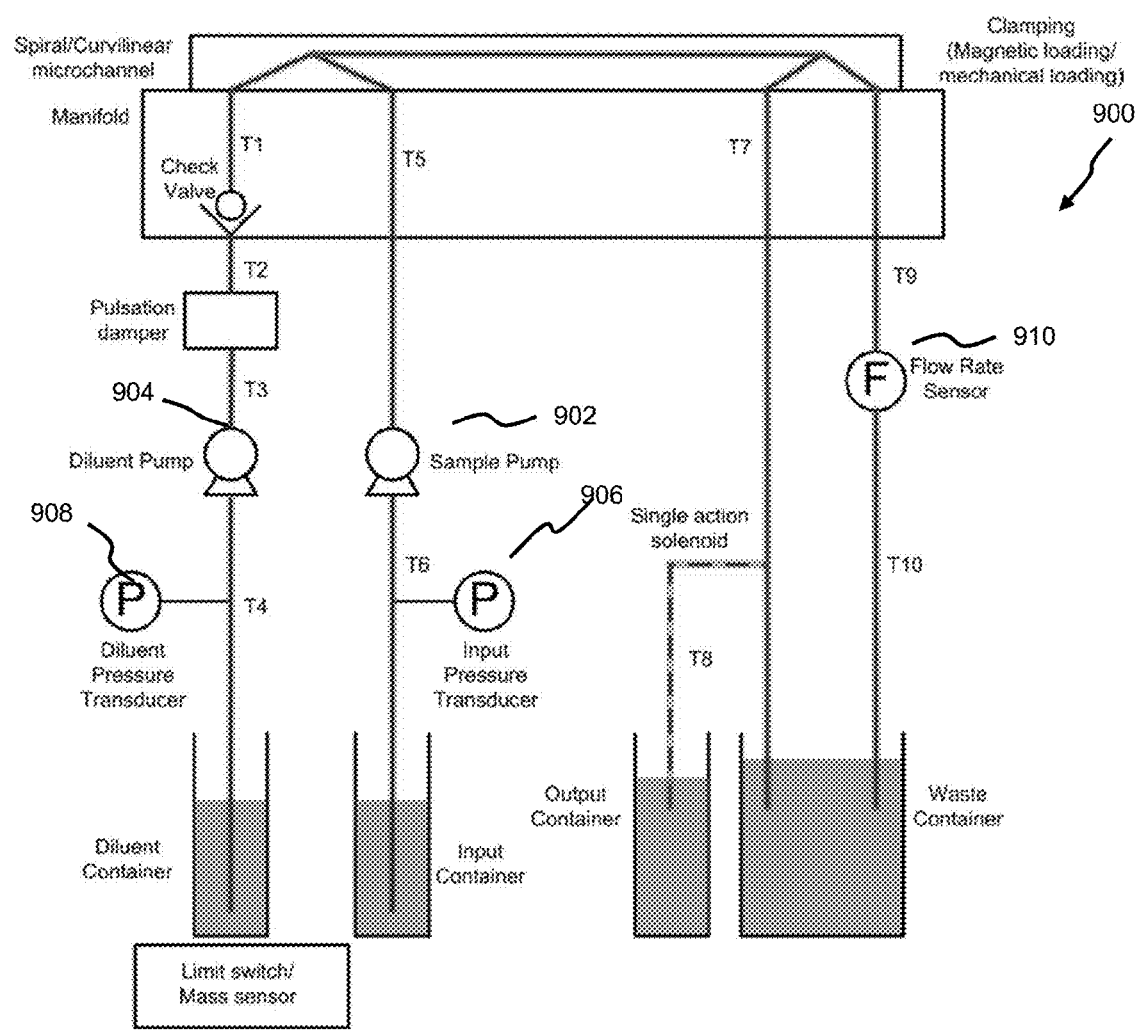
FIG. 9 id s schematic diagram of a diagnostic architecture in accordance with an embodiment of the present disclosure.

FIG. 9 shows a schematic diagram of the diagnostic architecture 900. The main control attributes provided are the two control signals sent to sample pump 902 and diluent pump 904. The fluid velocity is a velocity at which the combination of the diluent and sample flows in the curvilinear microchannel 502 or the spiral microchannel 602. This is controlled by setting the appropriate flowrate on the two pumps. Once the Radius of curvature is defined as in FIG. 7, the flow rate can then be adjusted to get the Dean cycle within a given channel length. Vice versa, the flow rate can be fixed and the channel radius and length can be selected based on the above equations. The pressure transducers 906, 908 help to detect if the microchannels have any blockage that can affect the separation quality. Increase in the pressure values over set threshold is detected as fault and the separation is stalled with the machine requiring a user action. Large blockages can increase the pressure within the system beyond safe limits and can results in biohazard spills as well as operator injuries. The pressure transducers 906, 908 help to prevent such accidents. As most pressure transducers do not have high sensitivity at low pressure ratings, the flow rate sensor 910 thus act as a redundant mechanism to verify whether the pumps are dispensing at the right flow rate as well as any blockages within the channel and the fluidic lines.

Figure 8A:
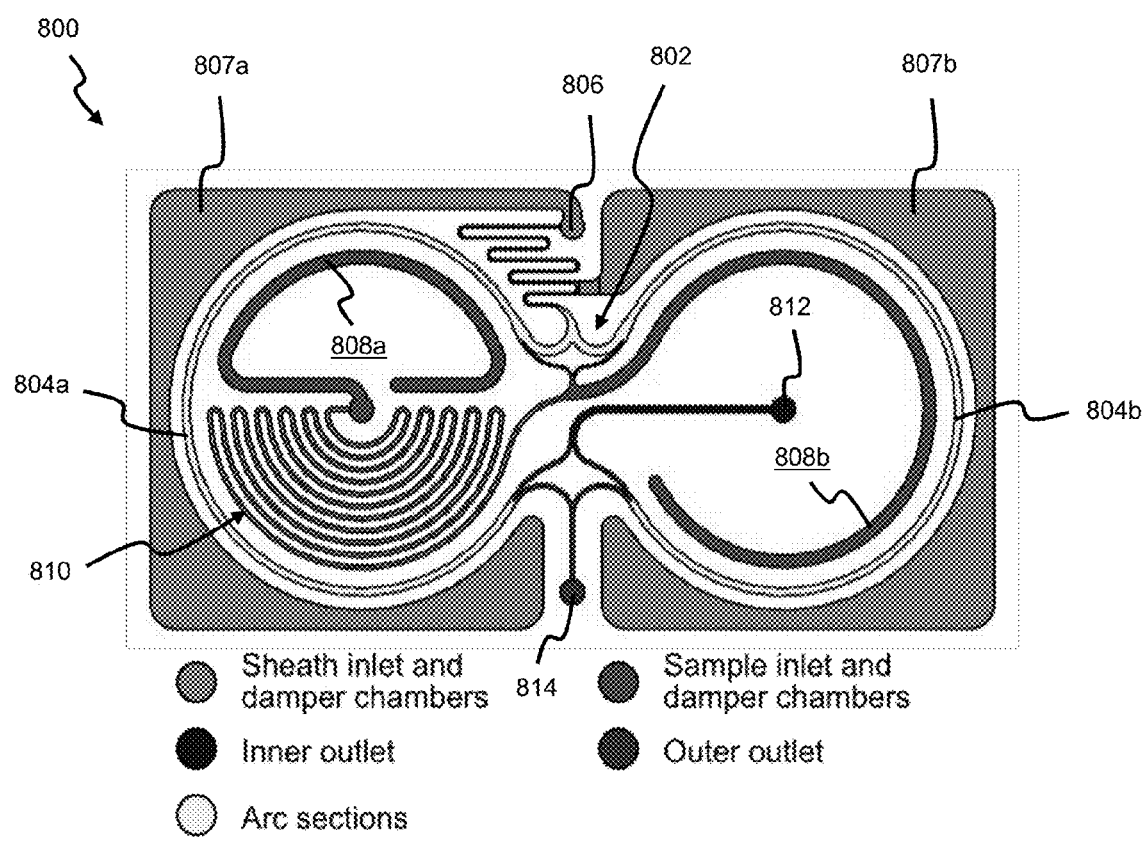
FIG. 8 shows a top view of a proposed biochip configured with a microchannel having two curvilinear sections coupled in parallel but in an opposing arrangement, in accordance with a further embodiment.

In accordance with yet another aspect, FIG. 8a shows a top view of a proposed biochip 800 configured with a microchannel 802 having two (first and second) curvilinear sections 804a, 804b (i.e. arc sections) coupled in parallel but in an opposing arrangement. The proposed biochip 800 is similarly arranged to be used in the diagnostic system as afore described, and is also replaceable after a number of usages (e.g. one time use). The microchannel 802 has a start end and a collection end, where samples and wastes can be introduced and collected respectively. The two curvilinear sections 804a, 804b are located at the start end of the microchannel 802. Specifically, the arrangement of the two curvilinear sections 804a, 804b are such that they are mirror reflections of each other. Indeed, this implies that the biochip 800 has a left and a right portion, from a top perspective view, as will be appreciated. In addition, the biochip 800 includes a sheath inlet 806 coupled to associated (first and second) damper chambers 807a, 807b, which are divided into two substantially similar portions, each 807a, 807b being positioned on the left and right portions of the biochip 800. The sheath inlet 806 is also directly coupled to the microchannel 802. Further, biochip 800 also includes two (first and second) sample inlets 808a, 808b (coupled to associated damper chambers) which are arranged as curvilinear portions with a predetermined length and width, each curvilinear portion positioned on the left and right portions of the biochip 800.

In this instance, the curvilinear portion of the first sample inlet 808a is arranged to be substantially semi-circular in shape, while the curvilinear portion of the second sample inlet 808b is arranged to be substantially C-shaped like. The second sample inlet 808b is directly coupled to the start end of the microchannel 802, whilst the first sample inlet 808a is indirectly coupled to the start end of the microchannel 802 via a high flow resistance channel section 810. The high flow resistance channel section 810 comprises a series of semi-circular microchannels in a winding arrangement. Also, the microchannel 802 has an inner outlet 812 and an outer outlet 814, branching from the collection end of the microchannel 802. Hence, on the left portion of the biochip 800, the first sample inlet 808a and high flow resistance channel section 810 are arranged to be encompassed by the first curvilinear section 804a, which is in turn encompassed by the first damper chamber 807a. On the other hand, on the right portion of the biochip 800, the second sample inlet 808b surrounds the inner outlet 812, and both of them are encompassed by the second curvilinear section 804b, which is in turn encompassed by the second damper chamber 807b. The outer outlet 814 lies in a spacing gap formed between the left and right portion of the biochip 800.

An advantage of the simple channel design of the proposed biochip 800 in this instance over the designs of FIGS. 5a and 6a is that it enables easy parallelization, allowing throughput to be doubled, which is found to be the highest demonstrated in its class compared to existing microfluidics systems. A method of isolating (and enriching) CTCs from the blood of an individual using the proposed biochip 800 is similar to the method 700 of FIG. 7, as afore described for the embodiments of FIGS. 5a and 6a, and thus for brevity sake will not be repeated. Another advantage is that the corresponding damper chambers coupled to the sheath and sample inlets 806, 808a, 808b, together with the curvilinear portions of the sample inlets 808a, 808b and the high flow resistance channel section 810 form an arrangement, which is functionally analogous to the RC π filters in IC design, and acts to stabilize the flow rate to advantageously enable use of pumps that have large pulsation, such as peristaltic pumps for delivery of the sample and sheath fluid. Thus, this provides a flow rate regulator feature, which with proper design of the volume of the damper chambers 807a, 807b (of the sheath inlet 806) and the fluid resistance offered by the high flow resistance channel section 810, enables the pulsation of the flow to be controllable to be within 1% to 5%.

It is to be appreciated that the purpose of providing the above flow rate regulator feature in this embodiment arises due to issues noted in existing systems. Currently, there are several methods for microfluidic sample delivery, such as using a syringe pump, a piston pump, a gear pump, a peristaltic pump, a piezoelectric micropump, or using a controllable pressure regulator. However, for biology sample, the complexity of the sample needs to be considered. The gear pump and piezoelectric pump, for example, will have detrimental effect on the cells in the sample during the pumping process. If the flow of the sample is driven solely by pressure difference, a flow rate is then determined by the structure of the fluidic system, and hence there is a high chance of fluctuations from a desired value with small disturbances such as blood clots. On the other hand, the syringe pump has a limitation in the volume of continuous delivery, while the piston pump is not cost effective in many cases. Considering the problem of sample contamination, system simplicity, flow controllability, consistency and continuity, use of the peristaltic pumping become the most appropriate. One issue for using the peristaltic pump is that the flow of the sample is not stable with periodic pulsations. In particular, the pulsation of the flow induced by the intermittent release of the rubber tubing will dramatically vary the flow profile, thus affecting the separation quality of the proposed biochip 800. Therefore, a solution to counter this problem is to include a filter/damper feature to regulate the flow rate of the peristaltic pump.

The channel dimension range for the device described in FIG. 8a is similar the device described in FIG. 5 The height of the channel can be in a range of between about 10 μm and about 200 μm, such as about 100 μm. 140 μm, 160 μm and about 175 μm. The width of the channel can be in a range of between about 100 μm and about 700 μm. The length of the channel can be in a range of between about 1 cm and about 100 cm.

Figure 8B:
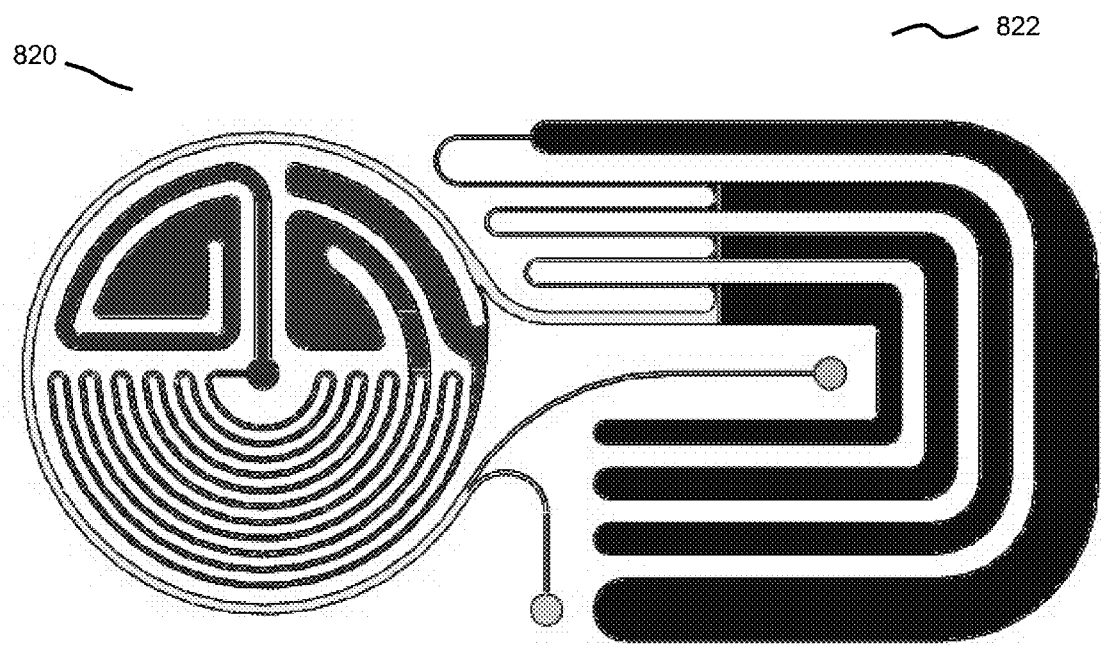

In an alternative embodiment to the biochip 800 of FIG. 8a, the microchannel 802 may have only one curvilinear section, for configuration simplicity, and the remaining features are the same as described above in relation to FIG. 8a. For example in FIG. 8b a single arc 820 with a damper 822 is shown.

In summary, the above embodiments describe proposed microfluidic devices having at least one curvilinear/spiral microchannel 502, 602 (with two inlets and two outlets), which is specifically devised to achieve cell/microparticle separation based on cell size and inertia. It is appreciated that one inlet is for introducing sample solution with cells/particles, the other inlet being for introducing cell/particle free buffer (i.e. sheath buffer), and one outlet is for collecting target cells/particles whereas the other outlet is for collecting waste comprising non-target cells/particles.

The curvilinear/spiral microchannel 502, 602 has an average radius of curvature $R_C$ and a hydraulic diameter $D_H$ such that under a flow rate $U_F$ of the fluid, the cells/particles with relatively small diameters are driven to one side of the channel cross-section under relatively high Dean drag force, whilst the relatively large cells/particles continue to stay at the opposite side under relatively low Dean drag force but subject to relatively high inertial lift force at a certain length $L_C$ of the curvilinear/spiral microchannel 502, 602.

Using the proposed design, it has been demonstrated that, as a possible example application, the microfluidic devices may used for isolating circulating tumor cells (CTCs) from blood cells at very high throughputs. The isolation of circulating tumor cells or CTCs from patient blood sample is essential for cancer diagnostics and therapy. During demonstrations, it has been shown that the proposed microfluidic device is able to isolate 99.999% of white blood cells from target CTCs from a 1.5× concentrated RBC depleted blood solution, which is driven to flow at a velocity of 0.25 mL/min. Further, by simply adding a parallel design that integrates two curvilinear sections in one biochip (i.e. refer to FIG. 8), the throughput may be doubled, thereby allowing 8 mL of blood sample to be processed in about ten minutes.

Hence, the proposed devices and method are suitable for isolating rare target cells from mixtures at high improved throughputs, and with extremely high purities to couple with downstream single cell or other molecular assays. Further applications that may be envisaged include, for example, cell separation from mixtures for disease diagnosis, in water filtration, for rapid solvent exchange and the like.

It is noted that in the design of FIG. 5a, the sample inlet is positioned at the inner side of the curvilinear microchannel 502, which results in the smaller cells to migrate in half Dean cycle, starting out from the inner channel walls to the outer wall walls. But as a variation to the design of FIG. 5a, an alternative design in FIG. 6a with the sample inlet now positioned at the outer side of the spiral microchannel 602 is also proposed. Particularly with this design, the larger cells migrate from the outer walls to the inner walls together with the smaller cells in the first half portion of the spiral microchannel 602 (i.e. lapsed of a half Dean cycle). But the larger cells are consequently inertial focused at the inner walls (according to the large inertial lift forces generated) which then allow them to be collected from the large cells outlet 608b (i.e. the inner outlet), whereas the smaller cells continue to migrate along with the Dean flow to the outer walls again after another half Dean cycle, and may be collected from the small cells outlet 608a (i.e. the outer outlet).

Advantages of the proposed microfluidic devices over existing microfluidics size-based cells/particles separation systems include the following:

(1). Throughput—Total Number of Cells/Particles Separated Per Minute

Due to their small sizes, existing microfluidics cells/particle separation systems are typically limited to low throughput due to the low flow rates that are characterized by those systems. In the proposed microfluidic devices, due to need for high flow rates to achieve effective separation, a processing throughput averaging about $5\times10^6$ cells/particles per minute may be attained. This throughput may be further increased by designing the curvilinear/spiral microchannels to have larger size cut-off, as a result of increasing the dimensions of the curvilinear/spiral microchannels.

(2). Issues Arising from Channel Clogging

Dimension of microchannels of most existing microfluidics systems are configured to be fairly small, and so channel clogging commonly occurs due to high concentration or cells/particle adsorption on the channel walls. In such situations, the separation resolution is also dramatically reduced due to change in the overall flow profile. In contrast, dimensions of the microchannels of the proposed microfluidic devices are configured to be in the 100's of microns range and hence, are not as susceptible to related issues arising from channel clogging.

(3). Separation Resolution as a Function of Throughput

A separation resolution for most existing microfluidics systems is inversely proportional to the flow rate (and hence the throughput). This means that, as the flow rate (and throughput) increases, the separation resolution diminishes. But in the proposed microfluidic devices, the separation resolution remains fairly constant even at high flow rates. Further, apart from flow rate, the concentration of cells/particles may also affect the separation resolution, due to increased particle-particles (or cell-cell) interactions. In this respect, the proposed curvilinear/spiral microchannels 502, 602 have fairly large channel dimensions and therefore may accommodate higher particle concentrations.

In terms of application for CTC isolation, the proposed microfluidic devices address a number of key concerns pertaining to existing CTC isolation methods. By way of background, current approaches for CTCs enrichment include density-gradient centrifugation, which produces a mononuclear fraction with CTCs due to their similar buoyant density and immuno-magnetic procedures using antibodies against adhesion molecules (such as EpCAM) that are commonly expressed on malignant epithelial cells. After enrichment, the CTCs are then identified using immunological assays for cytokeratins staining and molecular assays such as reverse transcription PCR (RT-PCR). Alternative techniques, such as flow cytometry, have also been developed to sort or enrich CTCs from peripheral blood. These methods are however complex, expensive, and usually require long processing time. As multi-step sample preparation is required, it may undesirably result in cell contamination or cell loss, thereby affecting the sensitivity of the cell assay result. Moreover, viability of CTCs is also lost as cell fixation and labeling are required for most of these current techniques.

In recent years, microfluidic approaches for CTCs separation and detection have emerged as an attractive alternative because it enables a fully enclosed and integrated system to be made for processing clinical samples, which beneficially helps to minimize sample loss, thus resulting in a more sensitive enumeration of CTCs. Presently, various microfluidic systems that utilize different separation principles, such as physical filtration using micro structures, dielectrophoresis, anti-EpCAM coated channels or micropillars or immuno-labeled super-paramagnetic particles have been applied for CTCs separation. However, problems commonly experienced for physical filtration include clogging issues and low sensitivity due to the heterogeneity of CTCs shape and size. In this regard, the dielectrophoresis technique is advantageous since it does not require labeling or chemical modification. However, the dielectrophoresis technique is limited by the small number of CTCs present and also by the similar dimensions of leukocytes with the CTCs. The use of surface molecules, for example EpCAM, is also not as desirable because the amount of EpCAM present often varies widely for different tumor types and therefore, retrieval of isolated CTCs may be difficult due to the cell binding in the microfluidic system.

With the above in mind, the proposed microfluidic devices and method 700 in FIG. 7 accordingly offer a couple of distinct advantages over existing microfluidic CTCs separation methods. Firstly, a continuous operating mode at a high flow rate (i.e. 0.8 mL of blood per minute) is attainable for the proposed microfluidic devices and method to enable faster processing of clinical samples (i.e. less than 10 minutes per 8 ml of whole blood). Also, no chemical modifications of channel or antibodies labeling is required for processing the blood sample using the proposed microfluidic devices and method, which further reduces processing time and costs, thereby facilitating use of the proposed microfluidic devices in resource limited situations. Moreover, as the dimensions of the curvilinear/spiral microchannel 502, 602 are configured to be fairly large, clogging issues are substantially (if not completely) eliminated in the proposed microfluidic devices. This beneficially increases the sensitivity of CTCs detection with high repeatability. Lastly, the proposed microfluidic devices allow easy collection of viable CTCs after separation in a single step, which makes it suitable for subsequent biological assays on the sorted CTCs.

CONCLUSIONS

A high throughput and highly sensitive technique to isolate viable rare-cells from blood is described using curvilinear channels. Inertial cell focusing is employed in the device to achieve size-based isolation of low abundance cells from blood. By tuning the dimensions of the curvilinear microchannels to achieve a force ratio ($i_F$) greater than 2 between inertial and Dean drag force, the larger particles/cells (in this case CTCs) are focused and collected from near the inner microchannel cross-section while the blood cells, with a force ratio ($i_F$) less than 2 are collected from the outer cross-section. As an application of the developed device, separation of CTCs from peripheral blood with high efficiency and throughput is demonstrated. The simple channel design allows for easy parallelization with the ability to analyze milliliters of clinical blood samples within minutes. Integrating chip-based detection downstream the device will provide a competent tool for clinical cancer diagnosis. Finally, a technique to integrate dampers into the microchannel design to achieve stable laminar flows is also described.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

The invention claimed is:
1. A microfluidic device comprising:
at least one inlet for receiving circulating tumor cells and other cells in a sample;
at least one curvilinear and/or spiral channel through which the sample is caused to undergo migration along at least a partial Dean vortex to isolate the circulating tumor cells from the other cells;
a flow resistance channel arranged to be coupled to the at least one inlet, the flow resistance channel comprising a series of microchannels to stabilise flow fluctuations;
and at least one outlet in communication with the at least one curvilinear and/or spiral channel for providing the isolated circulating tumor cells, wherein the at least one curvilinear and/or spiral channel is configured to provide a predetermined Force ratio greater than or equal to 2 based on a desired threshold cell size of the circulating tumor cells, the predetermined Force ratio being defined as a ratio of inertial lift force ($F_L$) to Dean drag force ($F_D$), and wherein the predetermined Force ratio is further defined according to the equation:

$$i_F = F_L/F_D = \frac{85.11 R_C a_C^3}{h^4},$$

where $i_F$ is the Force ratio, $R_c$ is the radius of curvature, $a_c$ is the cell size, and $h$ is the at least one curvilinear and/or spiral channel height, wherein the threshold cell size is about 15-20 μm.

2. The device of claim 1, wherein the device is comprised in a biochip in a microfluidic packaging configured as a disposable cartridge.

3. The device of claim 1, wherein the at least one curvilinear and/or spiral channel height is arranged to be smaller than ten times the threshold cell size.

4. The device of claim 1, wherein the at least one curvilinear and/or spiral channel has a cross-section having a channel width and a channel height defining an aspect ratio of the at least one curvilinear and/or spiral channel.

5. The device of claim 4, wherein the at least one curvilinear and/or spiral channel width is arranged to be approximately between 300 μm to 650 μm.

6. The device of claim 5, wherein the at least one curvilinear and/or spiral channel height is arranged to be approximately between 120 μm to 180 μm.

7. The device of claim 1, wherein the radius of curvature is configured to be approximately between 5 mm to 20 mm.

8. The device of claim 1, wherein the at least one outlet includes a first outlet and a second outlet to respectively enable the isolated circulating tumor cells and the other cells to be provided.

9. The device of claim 1, wherein a total length of the at least one curvilinear and/or spiral channel is arranged to be between 5 cm to 100 cm.

10. The device of claim 9, wherein the at least one curvilinear and/or spiral channel is an arc and the total length is configured to generate a half dean cycle migration.

11. The device of claim 9, wherein the at least one curvilinear and/or spiral channel is a spiral and the total length is configured to generate whole number multiples of a dean cycle migration.

12. The device of claim 1, wherein the at least one inlet includes a first inlet and a second inlet arranged to be coupled to respective damper chambers to regulate a flor rate of the sample the at least one curvilinear and/or spiral channel, wherein the first inlet is for introducing the sample into the at least one curvilinear and/or spiral channel and the second inlet is for introducing a sheath fluid into the at least one curvilinear and/or spiral channel.

13. A diagnostic system configured for detecting circulating tumor cells in a sample comprising: a microfluidic device according to claim 1 configured to isolate the circulating tumor cells from other biological cells in a sample; and a processor configured to generate a diagnostic indication based on the circulating tumor cells isolated by the microfluidic device.

14. A diagnostic system according to claim 13, wherein the sample is a whole blood sample or a red blood cell depleted blood sample.

15. A method of manufacturing a microfluidic device comprising:
providing at least one inlet for receiving circulating tumor cells and other cells in a sample, and at least one curvilinear and/or spiral channel through which the sample is caused to undergo migration along at least a partial Dean vortex to isolate the circulating tumor cells from the other cells;
providing a flow resistance channel arranged to be coupled to the at least one inlet, the flow resistance channel comprising a series of microchannels to stabilise flow fluctuations;
providing at least one outlet configured for communicating with the at least one curvilinear and/or spiral channel for providing the isolated circulating tumor cells; and
selecting a curvilinear and/or spiral channel height, radius of curvature, and length to provide a predetermined Force ratio greater than or equal to 2 based on a desired threshold cell size of the circulating tumor cells, the predetermined Force ratio being defined as a ratio of inertial lift force ($F_L$) to Dean drag force ($F_D$), and wherein the predetermined Force ratio is further defined according to the equation:

$$i_F = F_L/F_D = \frac{85.11 R_C a_C^3}{h^4},$$

where $i_F$ is the Force ratio, $R_c$ is the radius of curvature, $a_c$ is the cell size, and h is the curvilinear and/or spiral channel height, wherein the threshold cell size is about 15-20 μm.

* * * * *